United States Patent [19]

Blinkhorn

[11] Patent Number: 4,834,720
[45] Date of Patent: May 30, 1989

[54] IMPLANTABLE PORT SEPTUM

[75] Inventor: Francis E. Blinkhorn, Vernon, N.J.

[73] Assignee: Becton, Dickinson and Company, Franklin Lakes, N.J.

[21] Appl. No.: 137,645

[22] Filed: Dec. 24, 1987

[51] Int. Cl.⁴ .............................................. A61M 5/00
[52] U.S. Cl. ................................... 604/244; 604/175; 428/217
[58] Field of Search ................... 604/175, 244, 86, 87, 604/88, 198, 200, 201, 93; 215/247-250; 428/213, 217

[56] References Cited

U.S. PATENT DOCUMENTS 4,567,088  1/1986  Skogaan et al. .................... 428/217
4,698,061  10/1987  Makaryk et al. ................ 604/244 L
4,710,167  12/1987  Lazorthes ............................ 604/93

OTHER PUBLICATIONS

Port-A-Cath® brochure, a product of Pharmacia Hospital Products, Pharmacia Inc., Piscataway, NJ 08854, (revised Jan. 1985).
Mediport® brochure, a product of Cormed TM Inc., 591 Mahar St., P.O. Box 470, Medina, N.Y. 14103.

Primary Examiner—Stephen C. Pellegrino
Attorney, Agent, or Firm—Robert P. Grindle

[57] ABSTRACT

A septum is provided for use with implantable ports used for repeated drug delivery infusions. The septum allows for a substantially higher (more than twice) number of punctures prior to leakage and failure. This is achieved by the use of two different Shore A durometer hardnesses for different sections of the septum, one of harder material than used in prior art septums for the main body of the septum, and a section of much softer Shore A duromater hardness adjacent the inner surface of the septum for greater sealing facility when a needle is withdrawn. In addition, the greater hardness of the main body allows for greater stability of the needle when in place in the septum.

5 Claims, 2 Drawing Sheets

IMPLANTABLE PORT SEPTUM

Background and Description of the Invention

The present invention relates to an implantable device designed to permit repeated access to the vascular system of human beings without the trauma associated with commonly employed invasive techniques. The device which is implanted includes a self-sealing injection port, and the septum therefor is the object to which the present invention is specifically directed. The implantable device includes a delivery catheter for the receipt and delivery of the medications introduced into the implantable device. The introduction of solutions of various kinds into the implantable device is performed by needle injection, usually with a "Huber point" needle.

Thus, in those instances where individuals need to have repeated injections of some kind or another, the instant invention is directed to this kind of situation. The implantable device is shaped something like the shape of a volcano, and includes centrally thereof a septum for receiving the needle therethrough. The septum is designed to be resilient enough to receive sequentially a number of needle injections therethrough, while allowing for sealing of the area that the needle passed through, once the needle is withdrawn.

Usually the implantable device is arranged to be implanted in the individual in an area of the body convenient for the multiple infusions which will subsequently take place. Also, the place is selected so that the implanted device is as inconspicuous as possible, and is as undisturbed as possible by normal body movements.

As will be understood with devices of the kind discussed herein, it is important that the septum through which the needle is inserted for injections be such that it is a self-sealing material which effectively prevents any leakage, once the needle is removed therefrom. Ordinarily, the septum may be used for about 2,000 infusions. Thereafter, the septum deteriorates and leaks. One approach to this problem in the past has been to select dimensions for the septum which are greater than the port body housing so that the septum body is "precompressed" prior to use by being forced into the housing. This pre-compression has the effect of securing a self-healing or healing septum.

In the past, the material selected for septums has been an implantable grade silicone elastomer. The silicone material is selected to have a Shore A durometer which will meet two criteria. That is, it is stiff enough to receive and hold stable an implanted needle. Nevertheless, the material must be soft enough so as to have the desired resealing properties so that leakage does not occur after each infusion for the usual number of punctures which, as stated above, is about 2,000.

With this invention, by contrast, a septum is provided comprised of two different areas of implantable grade silicone elastomer. One area is the main body of the septum comprised of a material having a Shore A durometer of within the range of between about 65 and 80. Because of this, the body of the septum is stiffer than that usually used traditionally with septums of the prior art having a Shore A durometer in the range of 50-65. Because of this, the stiffer body of the septum of this invention has the ability to maintain a needle stablized much better than the prior art septums.

In addition to the main body of the septum of the invention herein being of an elastomer of a higher stiffer Shore A durometer material, the invention here contemplates the use of a portion of the septum in the area immediately adjacent the internal surface of the septum of an implantable grade silicone elastomer with a much softer Shore A durometer within the range of between about 10 and 35 Shore A durometer. Because of this, the much softer material has the effect of sealing (or self-healing, if you will) when the needle is withdrawn. In addition, only minimum "oversizing" of the septum dimensions are required, and as a result a lesser degree of compression is required to fabricate the unit of the invention with superior sealing qualities. Because of this, the device of the invention achieves significantly higher number of punctures (5,000 or more) prior to any failure and leakage.

In considering the materials generally useful for carrying out the invention here, one may note that the main body of the septum having the hard elastomer may be selected to have a Shore A durometer within the range of between about 45 and 90. Preferably, the range will be within the range of between about 65 and 80. Preferably, further, the material will be an implantable grade silicone elastomer, although practitioners-in-the-art will understand that other elastomers may be utilized, as well, as long as they possess the properties required for an implantable device.

With respect to the resealing portion of the septum of the invention, the soft portion, the range of Shore A durometer of the elastomer will be within the range of between about 5 and 50, and preferably within the range of between about 10 and 35. By providing a septum of two different portions of Shore A hardness materials, the compromise required in prior art septums is avoided and the desired properties which are diametrically opposite to each other for specific purposes, including the resealing property and the needle holding or stability property are achieved with the invention here in a single septum.

Other objects and advantages of this invention will be apparent from the following description, the accompanying drawings and the appended claims.

DESCRIPTION OF THE DRAWINGS

Referring to the drawings in which like reference characters refer to like parts throughout the several views thereof, FIG. 1 shows a plan view of the septum 10 of the invention. As can be seen in FIG. 1, septum 10 includes two parts, 12 and 14. The section 14 is inserted into the main body portion 12 of the septum and faces one side of the septum to provide for the superior sealing qualities of the invention herein with the section 14 facing internally in an implantable device in which the septum is inserted prior to implantation.

Figure 1:
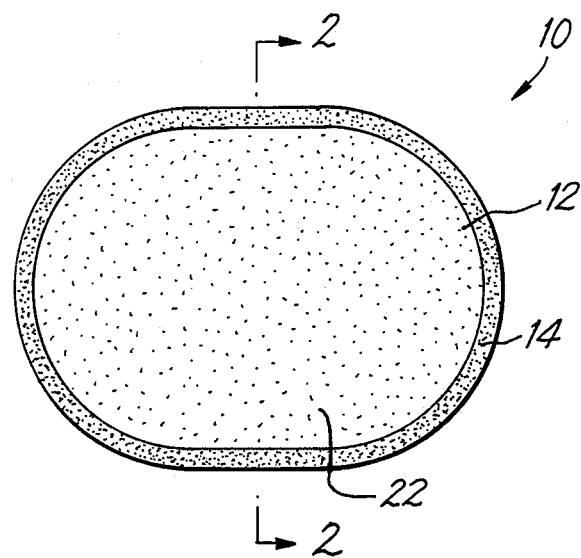
FIG. 1 is a plan view of the septum of the invention.
Figure 2:
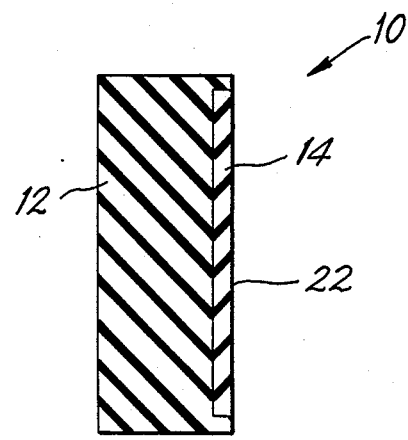
FIG. 2 is a sectional view of the septum of FIG. 1 taken along lines 2—2 of FIG. 1.

As can be seen in FIG. 2, the portion 14, which is of the much softer Shore A durometer elastomer, includes only a small portion of the septum body 10. Moreover, the portion 14 is "embedded" into and surrounded by the main body portion 12 except for the facing surface 22 of insert portion 14.

As purely illustrative of dimensions for the septum of the invention, the depth 16 of the septum body 10 is 0.27 inches. The depth of the softer insert 14 is 0.03 inches. The width dimension 20 of the body 10 is 0.750 inches, while the length of the septum is 1.00 inches. It will be understood, however, that these dimensions may vary depending upon the configuration of the implantable device utilizing the septum of the invention.

As purely illustrative of two totally implantable devices on the market in which the septum of the invention may be utilized, are PORT-A-CATH[R] a product of Pharmacia Hospital Products, Pharmacia Inc., Piscataway, N.J. 08854. A similar implantable device is MEDIPORT[R] a product of Cormed Inc., Medina, N.Y. 14103.

Thus, as will be appreciated from the above, there is provided in accordance with this invention, a septum for use with totally implantable devices for insertion in to the human body for repeated injections, as required. The septum of the invention avoids the compromises necessary with the prior art septum in that it utilizes a higher Shore A durometer elastomer to provide the main body of the septum and to provide enhanced needle stability during use.

Nevertheless, the septum of the invention has superior sealing qualities by utilizing a much lower Shore A durometer elastomer as the sealing portion of the septum adjacent the internal face of the septum when implanted, so that when a needle is removed from the infusion site the much softer elastomer seals much more rapidly and completely.

As a result, the invention herein provides for a much longer use period prior to the implantable device having to be removed from the body. This, of course, in turn, reduces substantially the invasion necessary to the human body in order to provide the facility of continued infusion of materials into the human body as required.

While the form of device herein described constitutes a preferred embodiment of the invention, it is to be understood that the invention is not limited to this precise form of device, and that changes may be made therein without departing from the scope of the invention which is defined in the appended claims. For example, the specific configuration of the insert of soft elastomer may be modified to provide, for example, an insert triangular in shape inserted into the body of the septum. The insert may be adhered to the main body portion of the septum by molding lamination techniques or an adhesive may be used, as long as the joining thereof is sufficient to hold the two parts together in use.

What is claimed is:
1. As septum for use in an implantable port device for repeated infusions of medication, characterized by
   (a) a substantially flat septum body;
   (b) said body having diametrically opposed faces forming a top surface and a bottom surface for said body;
   (c) an insert positioned in said bottom surface of said body;
   (d) said body being comprised of a substantially hard Shore A durometer implantable grade elastomer for stabilizing a needle inserted therein; and
   (e) said insert being comprised of a substantially soft Shore A durometer for resealing when a needle is inserted therethrough and withdrawn.
2. The septum of claim 1, further characterized by
   (a) said substantially hard Shore A durometer of said body is within the range of between about 45 and 90.
3. The septum of claim 1, further characterized by
   (a) said substantially soft Shore A durometer of said insert is within the range of between about 5 and 50.
4. The septum of claim 1, further characterized by
   (a) said substantially hard Shore A durometer of said body is within the range of between about 65 and 80; and
   (b) said substantially soft Shore A durometer of said insert is within the range of between about 10 and 35.
5. A septum for use in an implantable port device for repeated infusions of medication and the like, characterized by
   (a) a septum body;
   (b) said septum body comprised of two parts, a first part and a second part;
   (c) said first part of said body comprised of an elastomer of a substantially hard Shore A durometer;
   (d) said second part of said body comprised of an elastomer of a substantially soft Shore A durometer;
   (e) said first and second parts being laminated together to form said body;
   (f) said first part having a Shore A durometer of within the range of between about 65 and 80; and
   (g) said second part having a Shore A durometer of within the range of between about 10 and 35.

* * * * *